United States Patent [19]

Platsch

[11] Patent Number: 5,982,500
[45] Date of Patent: Nov. 9, 1999

[54] DEVICE FOR MEASURING THE SURFACE OF A PRINT PRODUCT

[76] Inventor: Hans Georg Platsch, Kupferstr. 20, D-70567 Stuttgart, Germany

[21] Appl. No.: 08/714,120
[22] PCT Filed: Dec. 29, 1995
[86] PCT No.: PCT/EP95/05157
   § 371 Date: Sep. 13, 1996
   § 102(e) Date: Sep. 13, 1996
[87] PCT Pub. No.: WO96/22518
   PCT Pub. Date: Jul. 25, 1996
[51] Int. Cl.$^6$ .................................................. G01N 21/45
[52] U.S. Cl. ............................................. 356/446; 356/429
[58] Field of Search ................................. 356/446, 429, 356/237

[56] References Cited

U.S. PATENT DOCUMENTS

| | | | |
|---|---|---|---|
| 4,950,905 | 8/1990 | Butler et al. | 356/446 |
| 5,053,822 | 10/1991 | Butler | 356/446 |
| 5,160,981 | 11/1992 | Hirashima | 356/446 |
| 5,216,469 | 6/1993 | Yamada | 355/246 |
| 5,276,481 | 1/1994 | Kinoshita et al. | 355/206 |
| 5,357,335 | 10/1994 | Sparks et al. | 356/446 |
| 5,519,497 | 5/1996 | Hubble, III et al. | 356/446 |

FOREIGN PATENT DOCUMENTS

| | | | |
|---|---|---|---|
| 3534973 | 4/1987 | Germany | G01N 15/00 |
| 1340218 | 12/1973 | United Kingdom | G01N 21/30 |

*Primary Examiner*—Robert H. Kim
*Assistant Examiner*—Zandra V. Smith

[57] ABSTRACT

A device for measuring the surface of a print product, has a measuring head including a measuring light source and measuring light detector. The measuring light source and the measuring light detector each have a directional characteristic, the axes of which are set at different angles relative to the surface of the print product so that if the surface of the print product is ideally level and smooth, no measuring light reaches the measuring light detector. The axes of the measuring light source directional characteristic and the measuring light detector directional characteristic coincide adjacent to the print product, and both form an angle of less than 90 degrees with the surface of the print product.

27 Claims, 6 Drawing Sheets

DEVICE FOR MEASURING THE SURFACE OF A PRINT PRODUCT

BACKGROUND OF THE INVENTION

1. Field of the Invention

The invention concerns a device for measuring the surface of a print product.

Such devices are used to determine the optical density of the different printing inks applied and generally have a measuring head which can be moved over the finished print product and determines the optical density of the different colour separations.

2. Disclosure of Relevant Art

Although, in modern printing machines, the ink films of the print products are dried by exposure to heat or light radiation so that the print products do not have to be dried in racks, even after such irradiation the printing inks are still somewhat tacky, so that print products stacked on top of each other can stick together. To prevent this, the upper surface of the print product is frequently dusted over with a fine powder, which may, for example, be finely ground mineral material or finely ground starch. The quantity of the powder mass applied is set on the dusting device according to empirical values and with continuous monitoring of the dusted products. However, with a more precise knowledge of the quantity of the powder mass actually obtained on the print product, it would be possible in many cases to reduce the powder delivery on the dusting device, i.e., to work with a smaller surplus. This would be advantageous not only in terms of a saving in powder, but it would also be possible in this way to prevent powder deposits in the printing machine which can result from the delivery of excessive powder.

SUMMARY OF THE INVENTION

The object of the present invention is to provide a device that can measure the powder mass deposited on the print product by dusting after printing.

This object is achieved, according to the invention, by a for measuring the surface of a print product, comprising a measuring head including a measuring light source and measuring light detector. The measuring light source and the measuring light detector each have a directional characteristic, the axes of which are set at different angles relative to the surface of the print product so that if the surface of the print product is ideally level and smooth, no measuring light reaches the measuring light detector. The axes of the measuring light source directional characteristic and the measuring light detector directional characteristic coincide adjacent to the print product, and both form an angle of less than 90 degrees with the surface of the print product.

The features of the invention are advantageous with respect to the largest possible variations in the sensor output signal with predefined variations in the mass of powder present on the print product.

The setting angle of the axis of the measuring light source characteristic relative to the surface of the print product is advantageously less than 45 degrees. The angle between the axes of the characteristic of the measuring light source and the measuring light detector is advantageously less than 45 degrees.

The wavelength of the measuring light source is selected to interact in different ways with the powder particles, on the one hand, and the printing ink, on the other hand. This provides for the sharpest possible differentiation between the measuring light modified by powder particles and those portions of the measuring light which are reflected by the printing base itself or by the printing ink present on the latter. The wavelength of the measuring light is preferably selected so that it is reflected by the powder particles but is absorbed by the printing ink or the printing base. Alternatively, it is possible to use a measuring light of a wavelength which releases a characteristic luminescence on the powder particles, whereas this is not the case with the printing ink and the printing base.

A device is provided for generating a flow of gas from the surface of the print product to the sensor spaced at a distance from the surface of the print product.

A device is provided for holding the flow of gas constant. Given a constant speed of flow of gas carrying the powder particles to the measuring section, it is possible for the size of the powder particles to be deduced from the output signal of a detector of the measuring section.

The device for generating a flow of gas includes a light transmitting measuring cell delimiting a part of the flow path that is near the sensor. This is advantageous in that the flow of gas carrying the powder particles is guided on a fully closed path. By this means, disturbance by ambient air is eliminated and the powder particles carried in the flow of gas can also be delivered to a filter in a controlled manner before the flow of gas is released.

The measuring cell has a measuring section having plane-parallel delimiting glass sheets. This geometry is advantageous with respect to its particularly simple and well-arranged optical ratios.

A measuring section of the measuring cell that works together with the sensor has a smaller flow cross section than a suction section that precedes it. This achieves a rate of flow of the gas in the measuring section which is of such a magnitude that no unwanted deposits are produced in the measuring section. A measuring cell which is thin in the direction of radiation is advantageous with respect to the measurement of the diameter of the powder particles since there are not several powder particles lying one behind the other in the direction of radiation.

A determination of the size and number of the powder particles is provided wherein the sensor has a bright-field or a dark-field beam path that is guided onto the detector. The output of the detector is connected to a counting circuit and/or a pulse width definition circuit, preferably through a signal shaping stage. The manner specified is reliable, does not require moving mechanical parts and can be easily evaluated by electronic means.

An evaluation unit works together with a memory storing the particle diameters assigned to the output signals of the pulse width definition circuits for different speeds of the flow gas. According to this feature, the interruption of the measuring light beam in the measuring section by the powder particles can be simply and rapidly converted into corresponding information on the diameter.

The measuring head is connected to a mouse and the measuring head output signal and the mouse output signal are both delivered to an evaluation circuit. This provides a very simple mechanical structure which nevertheless offers the possibility of measuring different areas of the print product with knowledge of the location of the sensor at any given instant.

The sensor has a strip of measuring light sources and measuring light detector elements and is guided to be displaceable normal to the longitudinal direction of the strip. This is advantageous with respect to a rapid and reliable measurement of large surface areas of a print product.

This can be effected automatically when the sensor can be moved in the guidance direction by a servodrive.

The measuring head is movable in two directions normal to each other, by means of servodrives. Thus, it is also possible to achieve accurate measurement of large surface areas of a print product without the expenditure of a large amount of time by the operator.

The sensor includes an image converter. The surface of the print product is projected onto the image converter through an optical system. This provides a particularly simple mechanical and electrical structure. It is therefore particularly suitable for a one hundred per cent inspection of all print products in a printing machine. Such a device can be disposed, for example, over the delivery table of the printing machine, with unimpeded access to the top side of the stack being assured with an appropriately selected focal distance for the optical system.

The image converter controls a display screen. In this way, the operator has direct information not only on the thickness of the dusting but also on its uniformity.

An evaluation unit is connected to the image converter and determines the number of converter pixels in which the brightness lies above or below a predefined brightness threshold. From the image generated instantaneously by the image converter from a dusted print product, the evaluation unit subtracts the pixels of a reference image previously generated by the image converter from an identical but non-dusted print product application measurement can also be represented as a numerical value.

A device according to the invention can also be used to measure the roughness of the surface(s) of a printing base. This information is important for the selection of the type and particle size of the powder used for dusting.

A method for printing and stacking print products according to the invention includes the steps of:

a) printing a print product with at least one printing ink;
b) depositing fine powder particles onto the print products, the print products being still wet with ink;
c) measuring the density of the powder particles deposited on the surface of the print product by providing:
   ca) a measuring head including a measuring light source and a measuring light detector,
   cb) said measuring light source and said measuring light detector each having a directional characteristic, the axes of which are set at different angles relative to the surface of the print product, intersecting adjacent to the print product.
   cc) the axes of the measuring light source directional characteristic and the measuring light detector directional characteristic both forming an angle of less than 90 degrees with the surface of the print product, so that if the surface onto which the fine powder is deposited on the print product was ideally level and smooth, no measuring light would reach the measuring light detector,
d) controlling the quantity of powder supplied as a function of the measured density of the powder deposited on the print product, and
e) stacking powdered print products. Advantageously, the method further includes the step of selecting the wavelength of the measuring light so that it interacts in different ways with the powder particles on the print product on one hand and with the printing ink or a surface of an unprinted printing base on the other hand.

BRIEF DESCRIPTION OF THE DRAWINGS

Preferred embodiments of the invention will now be described, taken together with the drawings, in which.

DETAILED DESCRIPTION OF THE PREFERRED EMBODIMENTS

Figure 1:
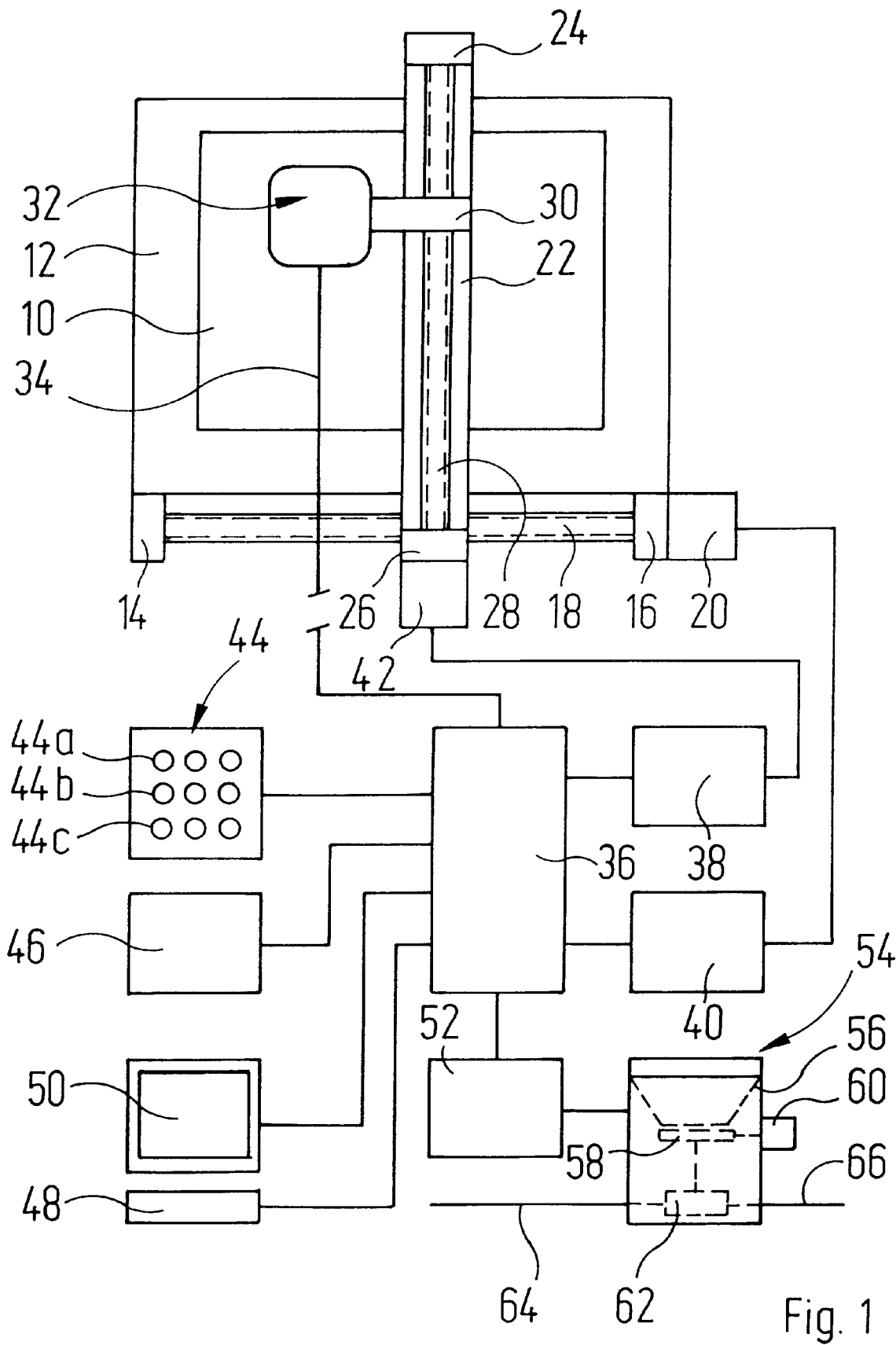
FIG. 1 shows a block diagram of a device for measuring the thickness of the powder dusting of a print product.

In FIG. 1, 10 denotes a finished print product which, following four-colour imprinting and dusting with a fine starch powder, has been laid on a measuring table 12. A threaded spindle 18, which is rotated by a stepping motor 20, is mounted on the lower longitudinal side of the measuring table 12 by means of bearing lugs 14, 16. The threaded spindle 18 works together with a threaded nut, not depicted in the drawing, of a bridge 22 which carries a further threaded spindle 28 by means of bearing lugs 24, 26. The threaded spindle 28, in turn, works together with a matched threaded nut provided on a retaining part 30. Mounted on the latter is a measuring head which is denoted as a whole by the reference 32. Details of different embodiments of the measuring head 32 are explained below with reference to the FIGS. 2–4.

In general terms, the functioning of the measuring head 32 is such that on a line 34 which, in practice, may be a trailing cable or a coiled cable, it provides a signal which corresponds to the density of the powder particles present on the surface of the print product 10. This signal is delivered to a control unit 36. The latter controls the stepping motor 20 through a driver circuit 38 and, through a further driver circuit 40, controls a stepping motor 42 which operates the threaded spindle 28.

A keypad 44 connected to a further input of the control unit 36 has three rows of keys 44a, 44b, 44c, on which are provided different preset inputs for the nature of the particular printing base used, the type of printing and the type of powder used for dusting. The last key in each of these rows of keys can be provided to measure the corresponding properties on a specimen, while the rest of the keys are used to select various predefined standard cases for which appropriate data are stored in a memory 46 which is likewise connected to the control unit 36. More precisely, different memory areas of the memory 46 each contain a characteristic, which assign to the surface dust application the output signals of the measuring head 32 obtained for a special printing base, type of printing and powder type, expressed, for example, in $g/m^2$. Some of these characteristics, with the measuring device, can be left to the discretion of the operator, some originating from printing jobs previously completed by the operator himself.

Further inputs can be entered into the control unit 36 from a keypad 48 and the density of the dusting derived by the control unit 36 for the input conditions from the data obtained on the line 34 using the characteristic stored in the memory 46 can be output on a display screen 50, as can other data which is of importance to the user.

The control unit 36, through a further driver circuit 52, can also control a dusting device, designated as a whole by the reference 54, provided for dusting the print products 10.

As indicated by the broken lines, the dusting device 54 has a dispensing hopper 56 with a delivery opening, provided at the lower end, under which a dosing plate 58 is disposed, separated vertically by a short distance. The dosing plate 58 can be moved with a controllable amplitude in the horizontal direction by a vibratory drive 60 and thus delivers a controllable stream of powder to a mixing element 62 which can operate, for example, in the manner of a water jet nozzle and whose inlet is connected to a compressed air line 64 while its outlet is connected to a powder line 66 which leads to a nozzle pipe extending, within the printing machine, transversely over the width of the print products.

Figure 2:
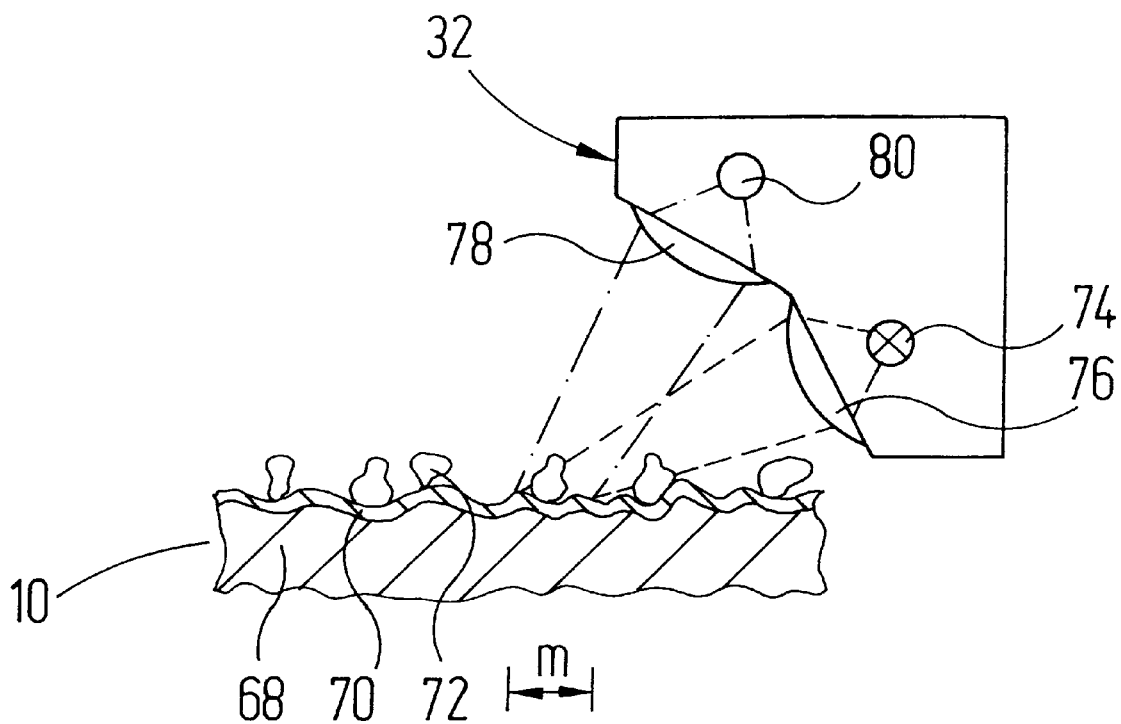
FIGS. 2–4 show modified measuring heads for use in the measuring device according to FIG. 1.
Figure 3:
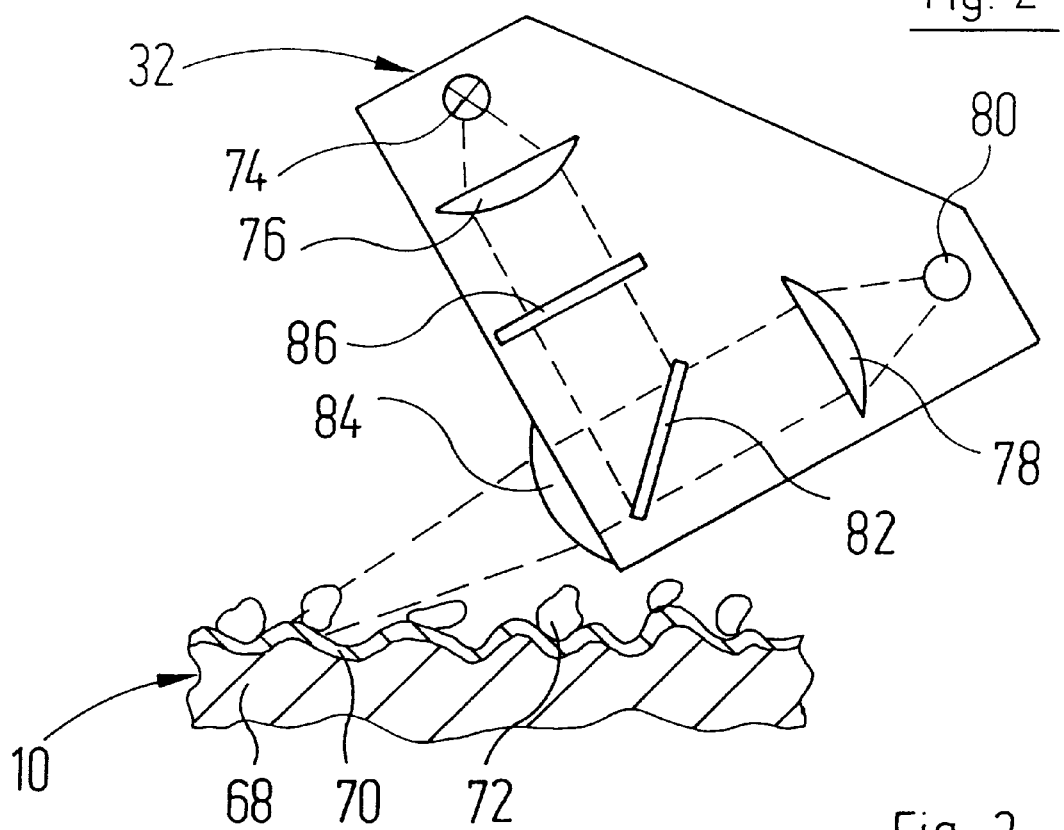
Figure 4:
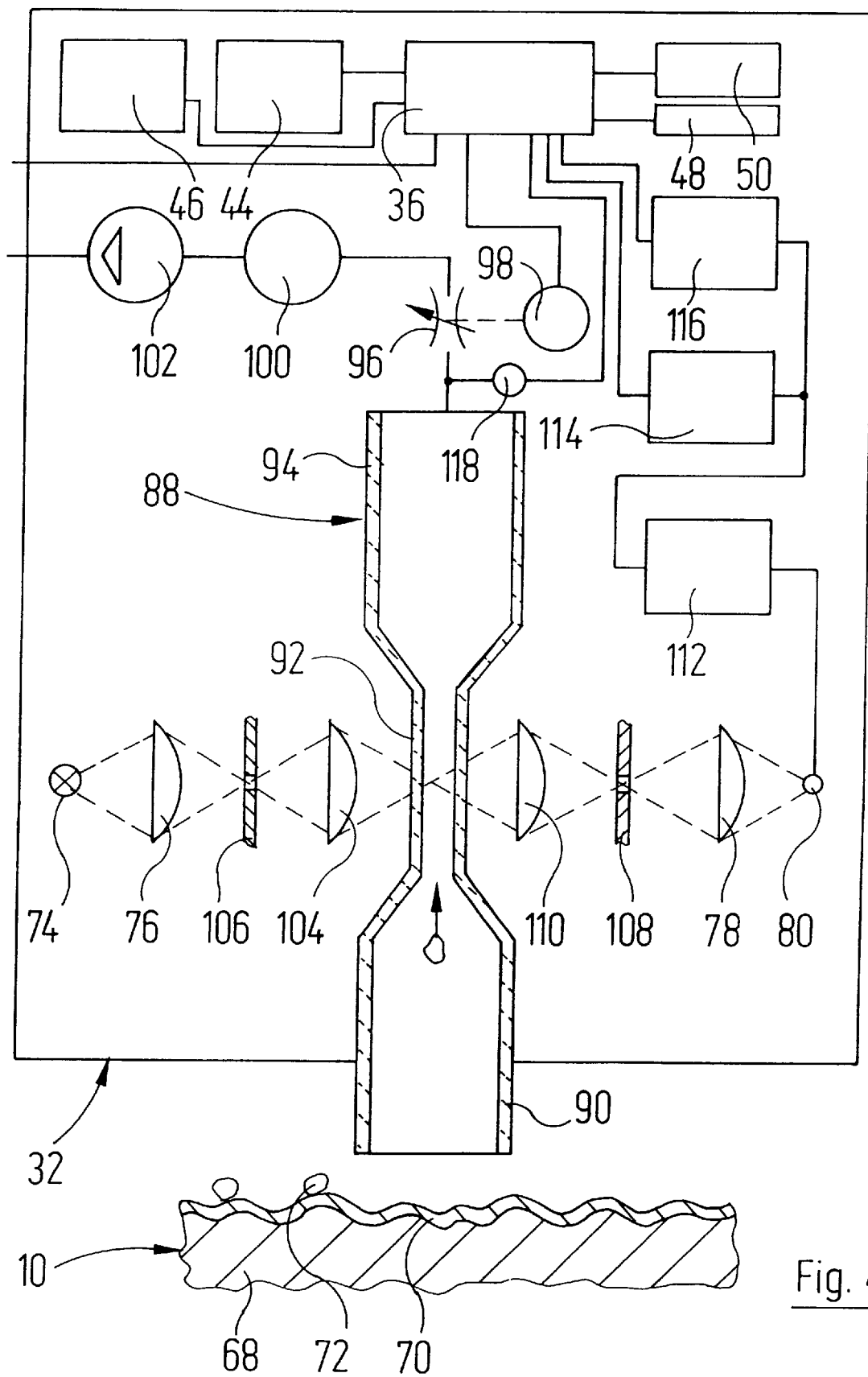

Reference is now made to FIGS. 2–4, in which a section of the printing base and each of the separate measuring heads 32 are not depicted in the same scale. The thickness of a printing base 68 and of an ink film 70 carried on it are also shown in enlarged scale, as is the size of powder particles 72 lying on the ink film.

As shown by FIGS. 2–4, the upper and lower sides of the printing bases 68 have peaks and troughs, the mean values for peaks and troughs not necessarily being the same for the two surfaces of the printing base. In general, the size of the powder particles 72 is selected so that their mean diameter is somewhat larger than the sum of the mean values for peaks and troughs on the two surfaces of the printing base, so that in the mean least favourable case (the troughs on the under side of a print product in alignment with the troughs on the upper side of the print product underneath it in the stack) the powder particles 72 carried by the lower print product still prevent the ink film 70 on the lower print product from coming into direct contact with the under side of the upper print product.

In the case of the measuring head 32 depicted in FIG. 2, the measuring light provided by a light source 74 is projected by means of a lens 76 on to a small measurement spot, having the dimension denoted as m, on the surface of the print product 10. As shown by FIG. 2, the incident beam path is directed towards the surface with as glancing an incidence as is consistent with the dimension of the lens 76. As shown by FIG. 2, the incident path of the measuring light source is directed towards the surface with a setting angle of less than 45 degrees.

Through a further lens 78, which is disposed as close as possible to the lens 76, the measurement spot m is projected on to a detector 80 which may be, for example, a light-sensitive diode or a phototransistor. As shown by FIG. 2, the angle between the incident beam path and the axis of the image projected onto the detector 80 is less than 45 degrees. And, the axis of the incident path of the measuring light source (the measuring light source characteristic) and the axis of the projected image path (measuring light detector characteristic) both form an angle of less than 90 degrees with the surface of the print product 10.

If the surface of the print product 10 were absolutely level and ideally smooth, then the light generated by the light source 74 would be reflected from the surface according to the reflection criteria and the lens 78 would not project any light whatsoever on to the detector 80. Due to the roughness of the surface of the printing base 68, which is exhibited in a corresponding roughness of the ink film 70, a small fraction of the light emitted by the light source 74 passes through the lens 78 on to the detector 80. The corresponding output signal of the detector 80 can be used directly to measure the roughness of the surface of the printing base 68 if the key located at the end of the key row 44a has been actuated to request such a measurement. If no such operation of the measuring device is required, then the control unit 36 extracts from the signal present on the line 34 a basic signal which corresponds to the roughness-induced part of the output voltage of the detector 80. After this differential formation, therefore, there still remains in the control unit a signal, as a measurement signal for the density of the powder dusting, which is produced by light fractions additionally diffused by the powder particles 72.

In the case of the modified embodiment example according to FIG. 3, elements whose function corresponds to elements already explained with reference to FIG. 2 are again denoted by the same reference number.

The axes of the lenses 76, 78 are set at right angles to each other and are brought together by a semi-transparent mirror 82. The lenses 76, 78 are selected so that before them there are parallel beams which are projected through a further lens 84 on to the surface of the print product 10.

In the case of the measuring head 32 according to FIG. 3, there is also a cut-off filter 86 set into the beam path by which the measuring light is delivered to the surface of the print product. This cut-off filter preferably has a passband range which selects out of the spectrum of the light source 74 such a wavelength that excites the powder particles to fluorescence or phosphorescence but does not so excite the ink film 70 and the printing base 68. Alternatively, such a wavelength can be selected that is reflected only by the powder particles 72 but is not reflected by the ink film 70 and the printing base 68. It is understood that the filter 86 is also transparent to the light returning from the printing base.

The measuring heads 32 shown in FIGS. 2 and 3 had measuring sections which worked by reflection. The measuring head depicted in FIG. 4 has a measuring section which works by transmission. To render this possible, although the printing base 68 is opaque, a special measuring cell is provided which is made from glass and denoted as a whole by the reference number 88. This measuring cell has a lower cylindrical suction section 90 which is moved over the surface of the print product 10 at a short distance from it, a flattened central measuring section 92 with plane-parallel delimiting walls, and an upper delivery section 94. The latter is connected to the suction side of a small suction pump 102 through an adjustable throttle 96, which can be actuated by a servomotor 98, and through a filter 100. The air flow generated by the suction pump 102 draws off at least a predefined portion of the powder particles 72 from the surface of the print product 10 and, within the thin air curtain in the measuring section 92, the individual powder particles pass through the measuring light beam generated by the light source 74. This measuring light beam is projected on to the path of the powder particles 72 through an intermediate projection lens 104 and a pinhole diaphragm 106, as well as the lens 76, while the lens 78 focuses the measuring light on to the aperture of a further pinhole diaphragm 108 which is then, in turn, projected on to the detector 80 through a second intermediate projection lens 110.

The output signal of the detector 80 is delivered to a signal shaping stage-112, and its output signal is sent to both a pulse width definition circuit 114 and a counting circuit 116. The pulse width definition circuit defines the distance between a trailing edge and a succeeding rising edge in the output signal of the signal shaping stage 112, i.e., the time interval within which the measuring beam path was interrupted by a powder particle 72. The speed of motion of the powder particles being known, the dimension of the powder particles is obtained from this time interval.

The output signals, corresponding to the size and number of the powder particles, from the pulse width definition circuit 114 and the counting circuit 116 are again delivered to a control unit 36. A further input of the latter receives the output signal of a pressure sensor 118 which is connected to the upper end of the measuring cell 88. The output signal of the pressure sensor 118 is indirectly a measure of the speed at which the powder particles 72 are drawn through the measuring cell 88 by the air flow. The control unit 36 controls the servomotor 98 so that the output signal of the pressure sensor 118 is held on a preset required value.

It is understood that, instead of the bright-field method described above for the detection of powder particles, it is also possible to use a dark-field method whereby the passage of a powder particle through the measuring section results in an augmentation of the output signal of the detector 80 rather than in a reduction of the output signal. The pulse width circuit 114 must then calculate accordingly the distance between a rising edge and the succeeding trailing edge in the output signal of the signal shaping stage 112.

Figure 5:
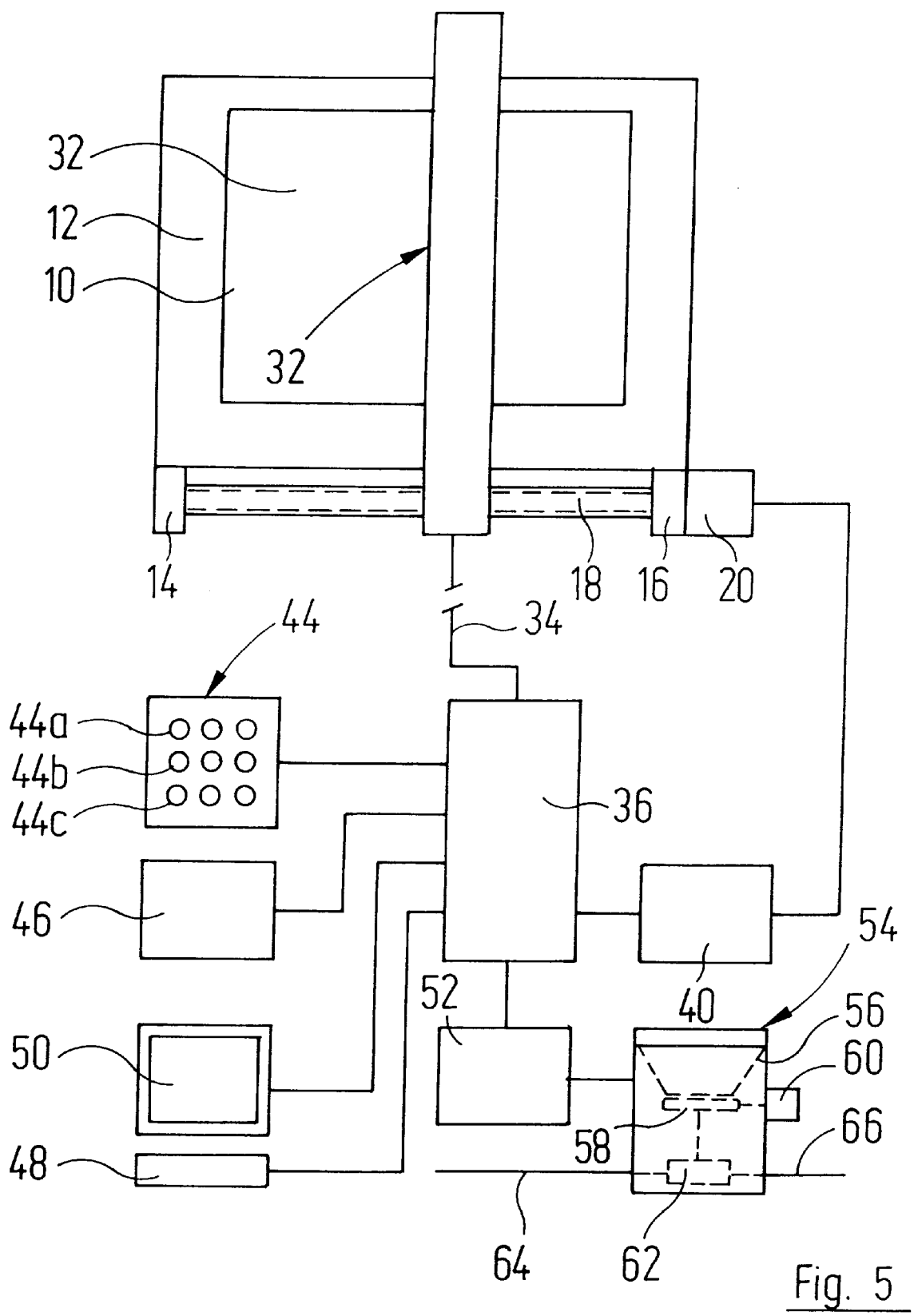
FIGS. 5–7 show block diagrams which are similar to FIG. 1, but which depict modified measuring devices.

In the case of the measuring device depicted in FIG. 5, the measuring head 32 has the form of a strip, extending over the full height of the measuring table 12 and being provided, at small intervals, for example of 5 mm, with a multiplicity of light barriers which work by reflection and have essentially the same structure as that shown in FIG. 2. Such a light barrier arrangement can be easily realized, for example with the use of light diodes and phototransistors, with its housing being made from a light-transmitting refractive material and with the lens 76 or 78 being incorporated directly into the outside face of the housing.

In the case of the measuring device according to FIG. 5, therefore, the y-direction servo drive can be omitted since the strip type measuring head 32 provides, in parallel, the output data of a larger number of measuring light barriers distributed in the y-direction.

Figure 6:
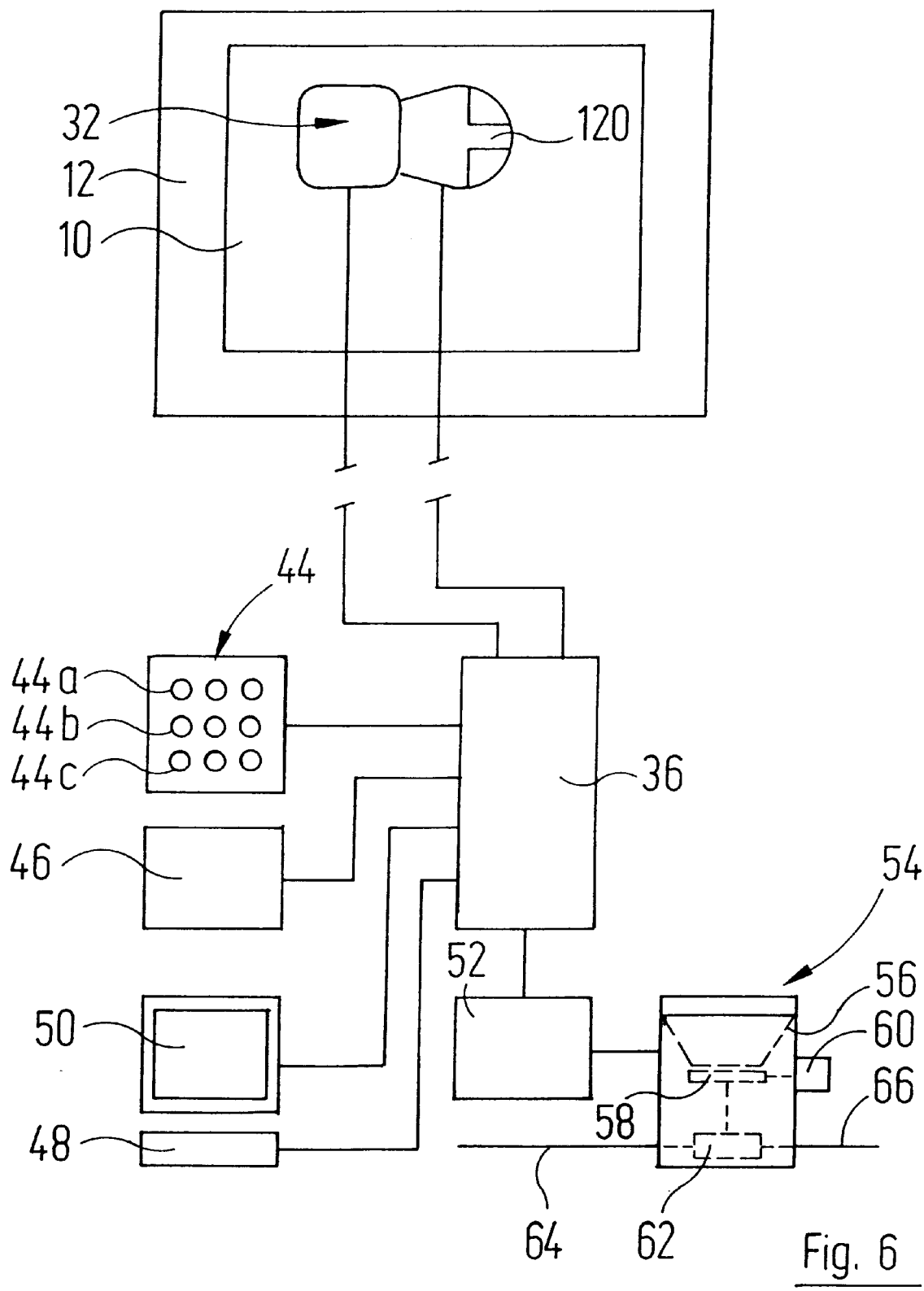

In the ca se of the embodiment example according to FIG. 6, a measuring head 32, which has a structure similar to those represented in FIGS. 2–4, is mechanically connected to a mouse 120, such as that known for the entering of data to personal computers. By adding up the position pulses emitted by the mouse, the control unit 36 can determine over which point of the print product 10 the measuring head 32 is located at a given instant.

The control unit 36 shows continuously on th e display screen 50 the powder density determined over, for example, the last ten path increments signalled by the mouse 120 and the powder density determined over the total travel. Alternatively, the control unit 36 can display on the screen the manually effected travel of the measuring head 32 signalled by the mouse 120 and in each case it can visually display the density of the dusting by means of the density and/or colour of the image point.

Figure 7:
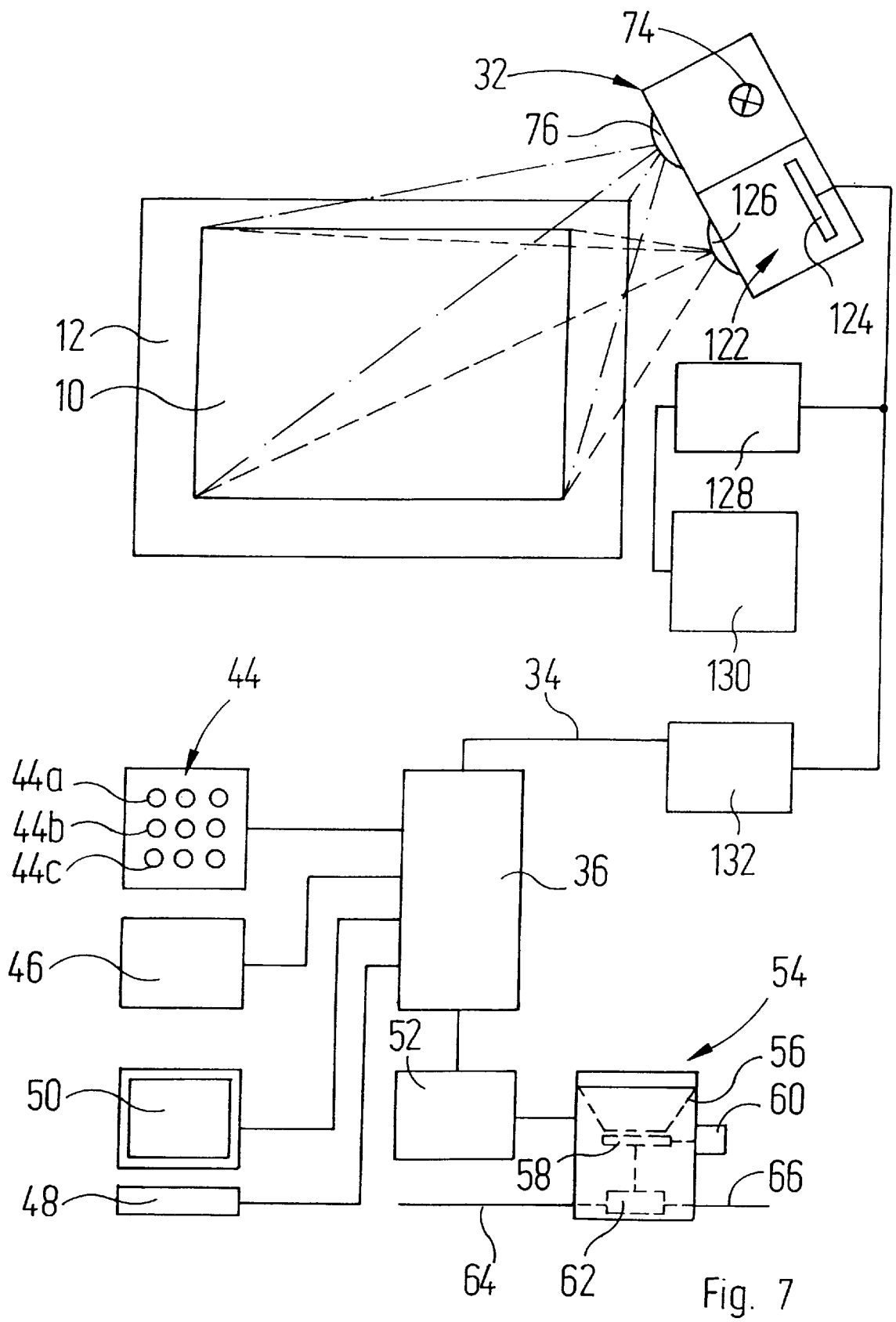

In the case of the embodiment example according to FIG. 7 (depicted in distorted perspective) there is disposed over the measuring table 12 a light source 74 which, in reality, is located in the vertical centre plate of the measuring table 12 and, as viewed from the side, illuminates the print product 10 in a manner similar to that of the measuring head according to FIG. 2. Mounted on to the housing of the light source 74 it a camera unit 122 which has an image converter 124 of the type usually used for TV cameras and also an optical system 126 which projects the entire print product 10 on to the image converter 124.

The image converter 124 is connected, through a driver card 128, to a display screen 130 which, in the brightness and/or colour of its separate pixels, provides a direct visual display of the dusting of the print product 10.

The image converter 124 is additionally connected to an evaluation card 132 which evaluates the brightness of the different pixels of the image converter 124. The evaluation card 132 can be programmed so that, for example, it interprets white image areas on the image converter 124 as diffused light from powder particles if the diameter of the spot is smaller than a predefined number of pixels (e.g. 3 pixels), while larger white image areas are interpreted as non-printed areas of the print product 10 (if the printing base is white). Thus, by counting the white image areas of the image generated on the image converter 124 which meet the powder particle criterion, it is possible to derive a measure of the dusting of the print product 10 which is transmitted to the control unit 36.

Alternatively, the evaluation card 132 can be designed so that it has a memory in which are stored all image pixels delivered by the image converter 124 when there is a non-dusted print product on the measuring table 12. In measuring a dusted print product 10, the evaluation card 132 then constructs the difference between the image pixels then delivered by the image converter 124 and the image pixels of the reference image stored in the memory, and this difference is again a measure of the dusting of the print product.

The dusting distribution can then again be output in visual form on the display screen 50 by the control unit 36 so that the operating personnel receive easily comprehensible information on the uniformity of the dusting and its deviations from a setpoint value. In addition, the control unit 36 can output on the display screen 50 the mean value of the dusting ascertained on the print product 10 and, in accordance with this mean value, effect an adjustment of the oscillation amplitude of the vibratory drive 60.

If a measuring head 32 such as that depicted in FIG. 7 operates with a measuring light wavelength with which the powder particles have a behaviour which is optically significantly different from the ink film 70 and the printing base 68 then, in the case of the measuring device shown in FIG. 7, the measuring head 32 can be mounted symmetrically over the vertical centre axis of the measuring table 12 so that a distortion-free image of the print product 10 is obtained on the image converter 124.

A measuring device according to FIG. 7 has a simple mechanical structure and the measuring head 32 can be disposed at a greater distance above the print product 10 to be measured, small vertical positional variations of the print product 10 not resulting in any significant impairment of the measurement result if the focal distance selected is appropriate for the optical system 126. Such a measuring device can thus be used for continuous control of the dusting in the actual production process, e.g. by mounting it on the delivery table of the printing machine, over the stack of sheets which is the process of being formed.

I claim:

1. Device for measuring the density of fine powder deposited on the surface of a printed product (10), comprising:

a measuring head (32) including a measuring light source (74) and a measuring light detector (80, 124), the measuring light source (74)and the measuring light detector (80, 124) each having a directional characteristic, the axes of which are set at different angles relative to the surface of the print product (10), the axes of the measuring light source directional characteristic and the measuring light detector directional characteristic intersecting adjacent to the print product (10), the axis of the measuring light source directional characteristic and the axis of the measuring light detector directional characteristic both forming an angle of less than 90 degrees with the surface of the print product (10), so that if the surface onto which the fine powder is deposited on the print product (10) was ideally level and smooth, no measuring light would reach the measuring light detector (80), the setting angle of the measuring light source directional characteristic relative to the surface of the print product (10) being less than 45 degrees.

2. Device according to claim 1, characterized in that the angle between the axes of the characteristics of the measuring light source (74) and the measuring light detector (80) is less than 45°.

3. Device according to claim 1, characterized in that the axis of the measuring light source and the axis of the measuring light detector are brought together by means of a semi-transparent mirror (82).

4. Device according to claim 1, characterized in that the wavelength of the measuring light is selected so that it interacts in different ways with the powder particles on the one hand and with the printing ink or the surface of an unprinted printing base (68) on the other hand.

5. Device according to claim 1, characterized by a device (88–102) for generating a flow of gas from the surface of the print product (10) to the sensor (74–80) disposed at a distance from the surface of the print product (10).

6. Device according to claim 1, characterized in that the measuring head (32) is connected to a mouse (120) and the measuring head output signal and the mouse output signal are both delivered to an evaluation unit (36).

7. Device according to claim 1, characterized in that the sensor (70–74) has a strip of measuring light sources and measuring light detector elements and is guided so as to be capable of displacement normal to the longitudinal direction of the strip.

8. Device according to claim 4, characterized in that the sensor (70–74) is capable of being moved in the direction of guidance by a servo drive (18, 20).

9. Device according to claim 1, characterized in that the measuring head (32) is capable of being moved in two directions normal to each other by means of servo drives (18, 20; 28, 42).

10. Device according to claim 1, characterized in that the sensor comprises an image converter (124) on to which the surface of the print product (10) is projected through an optical system (126).

11. Device according to claim 10, characterized by a display screen (130) which is controlled by the image converter (124).

12. Device according to claim 11, characterized by an evaluation unit (132) which is connected to the image converter (124) and determines the number of converter pixels in which the brightness lies above or below a pre-defined brightness threshold.

13. Device according to claim 12, characterized by an evaluation unit (132) which is connected to the image converter (124) and, from the image generated instantaneously by the image converter from a dusted print product (10), subtracts the pixels of a reference image previously generated by the image converter from an identical but non-dusted print product (10).

14. Use of a device according to claim 1 for measurement of the roughness of the surface of a printing base (68) to be printed.

15. Device according to claim 1, in which the measuring light source (74) and the measuring light detector (80; 124) are combined in a single measuring head (32).

16. Device for measuring the surface of a print product (10) with a measuring head (32) including a sensor (74; 80) responsive to powder particles (72), comprising a device (88; 102) for generating a flow of gas from the surface of the print product to the sensor (74; 80) spaced at a distance from the surface of the print product (10).

17. Device according to claim 16, characterized by a device (36, 96, 98, 118) for holding the flow of gas constant.

18. Device according to claim 16, characterized in that the device for generating a flow of gas comprises a light-transmitting measuring cell (88), delimiting a part of the flow path, near to which the sensor (74–80) is disposed.

19. Device according to claim 18, characterized in that the measuring cell (88) has a measuring section (92) having plane-parallel delimiting glass sheets.

20. Device according to claim 18, characterized in that a measuring section (92) of the measuring cell (88) which works together with the sensor (74–80) has a smaller flow cross section than a suction section (90) which precedes it.

21. Device according to claim 16, characterized in that the sensor (70–74) has a bright-field or a dark-field beam path which is guided on to the detector (80) and that the output of the detector (80) is connected to a counting circuit (116) and/or a pulse width definition circuit (114), preferably through a signal shaping stage (112).

22. Device according to claim 21, characterized in that an evaluation unit (36) works together with a memory (46) in which are stored, for different speeds of the flow of gas, the particle diameters assigned to the output signals of the pulse width definition circuit (114).

23. Device for measuring the surface of a print product, with a measuring head (32) including a sensor (80; 122), in which the sensor (74–80) is responsive to fine powder particles (72) and comprises a measuring light source (74) and a measuring light detector (80; 124), the measuring light source (74) and the measuring light detector (80) each have a directional characteristic the axes of which are set at different angles relative to the surface of the print product (10) so that, if the surface onto which the fine powder particles are deposited on the surface of the print product (10) was ideally level and smooth, no measuring light would reach the measuring light detector (80), and a setting angle of the measuring light source characteristic relative to the surface of the print product (10) is less than 45°.

24. Device for measuring the surface of a print product, with a measuring head (32) including a sensor (80; 122), an evaluation unit (36) and a mouse (120), in which the sensor (74–80) is responsive to fine powder particles (72), the measuring head (32) is connected to the mouse (120) and the measuring head output signal and the mouse output signal are both delivered to the evaluation unit (36).

25. Device for measuring the surface of a print product, with a measuring head (32) including a sensor (80; 122), and an optical septum (126) in which the sensor (74–80) is responsive to fine powder particles (72) and comprises a measuring light source (74), a measuring light detector (80; 124), an image converter (124) on which the surface of the print product (10) is projected through said optical system (126), and a display screen (130) that is controlled by the image converter (124).

26. Method for printing and stacking print products comprising the steps of:
   a) printing a print product with at least one printing ink;
   b) depositing fine powder particles onto the print product, the print product being still wet with ink;
   c) measuring the density of the powder particles deposited on the surface of the print product by providing
      ca) a measuring head including a measuring light source and a measuring light detector, cb) said measuring light source and said measuring light detector each having a directional characteristic, the axes of which are set at different angles relative to the surface of the print product, intersecting adjacent to the print product, cc) the axes of the measuring light source directional characteristic and the measuring light detector directional characteristic both forming an angle of less than 90 degrees with the surface of the print product, so that if the surface onto which the fine powder is deposited on the printed product was ideally level and smooth, no measuring light would reach the measuring light detector, d) controlling the quantity of powder supplied as a function of the measured density of the powder deposited on the print product, and e) stacking powdered print products.

27. The method according to claim 26, comprising the step of selecting the wavelength of the measuring light so that it interacts in different ways with the powder particles on the print product on one hand and with the printing ink or a surface of an unprinted printing base on the other hand.

\* \* \* \* \*